US00PP09330P

United States Patent [19]

Zary

[11] Patent Number: Plant 9,330

[45] Date of Patent: Oct. 17, 1995

[54] HYBRID TEA ROSE PLANT NAMED 'JACCOGEL'

[75] Inventor: Keith W. Zary, Thousand Oaks, Calif.

[73] Assignee: Bear Creek Gardens, Inc., Medford, Oreg.

[21] Appl. No.: 366,246

[22] Filed: Dec. 28, 1994

[51] Int. Cl.[6] ..... A01H 5/00

[52] U.S. Cl. ..... Plt./17

[58] Field of Search ..... Plt./11, 16, 17

*Primary Examiner*—Howard J. Locker

*Attorney, Agent, or Firm*—Klarquist Sparkman Campbell Leigh & Whinston

[57] ABSTRACT

A hybrid tea rose plant characterized by its coral orange flower color; its thick, leathery petals; its vigorous, upright habit of growth; its dark green, glossy foliage; and its good vase life.

1 Drawing Sheet

The present invention relates to a new and distinct variety of rose plant of the hybrid tea class which was originated by me by crossing the variety JACyap, unpatented, with the variety AnKORi, U.S. Plant Pat. No. 5,012.

The primary objective of this breeding was to produce a new rose variety having the excellent upright, vigorous growth habit and long stems of the female parent combined with the thick petals and good vase life of the male parent. The objective was substantially achieved, along with other desirable improvements, as evidenced by the following unique combination of characteristics that are outstanding in the new variety and that distinguish it from its parents, as well as from all other varieties of which I am aware:

1. Dark green, glossy foliage;
2. Vigorous, upright habit of growth;
3. Thick, leathery petals;
4. Good vase life; and
5. Novel coral orange flower color.

Asexual reproduction of this new variety by budding, as performed at Wasco, Calif., shows that the foregoing and all other characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color description using terminology in accordance with The Royal Horticultural Society (London) Colour Chart, except where ordinary dictionary significance of color is indicated.

Parentage:

*Seed parent.*—JACyap, unpatented.

*Pollen parent.*—AnKori, U.S. Plant Pat. No. 5,012.

Classification:

*Botanical.*—Rosa hybrida.

*Commercial.*—Hybrid tea.

FLOWER

Observations made from specimens grown in a greenhouse environment at Somis, Calif. in March through Jul., 1994.

Blooming habit: Continuouse.

Bud:

*Size.*—1½ to 1¾ inches long when the petals start to unfurl.

*Form.*—The bud form is long, pointed ovoid.

*Color.*—When sepals first divide, bud color is Red Group 38B. When half blown, the upper sides of the petals are Red Group 41C; and the lower sides of the petals are Red Group 38B.

*Sepals.*—Color: Green Group 143B. Surface texture: Covered in fine hairs. There are three normally appendaged sepals. There are two unappendaged sepals with hairy edges.

*Receptacle.*—Color: Green Group 143A. Shape: Funnel. Size: Medium, broad, 7/16 inch ×½ inch. Surface: Smooth.

*Peduncle.*—Length: Medium, 3 to 3½ inches. Surface: Glandular. Color: Medium green. Strength: Stiff, erect.

Bloom:

*Size.*—Large. Average open size is 4½ to 5 inches.

*Borne.*—Singly.

*Stems.*—Long, strong. Average length is about 22 to 26 inches.

*Form.*—When first open: High center. Permanence: Retains its form to the end, outer petals curl back.

*Petalage.*—Number of petals under normal conditions: 30.

*Color.*—The upper side of the petals is Red Group 41C. The reverse side of the petals is Red Group 38B. The base of each petal was a small (¼ inch×¼ inch), yellow (Yellow Group 4B) half moon at the point of attachment. The major color on the upper side is Red Group 41C.

*Variegations.*—Occasional white streak down the center of the guard petals.

*Discoloration.*—The general tonality at the end of the first day: No change. At the end of the third day: No change. On the plant, by day five, there is fading to Red Group 41D. There is no change in the cut flower held in water.

*Fragrance.*—Slight.

Petals:

*Texture.*—Thick, leathery.

*Shape.*—Round to slightly deltoid.

*Form.*—Tips slightly recurved, edges slightly to moderately quilled.

*Arrangement.*—Imbricated, with few petaloids in the center.

*Persistence.*—Drop off cleanly.

*Lastingness.*—On the plant: Long (7 to 8 days). As a cut flower: Long (9 to 10 days).

Reproductive parts:

*Anthers.*—Size: Medium. Quantity: Many. Color: Yellow. Arrangement: Regular around styles.

*Filaments.*—Color: Yellow.

*Pollen.*—Color: Lemon yellow.

*Styles.*—Color: Red.

*Stigmas.*—Color: Greenish white.

Form: Bush.

Growth: Vigorous, upright, branching. At one year, in the greenhouse, plants are 6 feet tall by 4 feet wide, producing 180 stems per square meter.

Foliage: Number of leaflets on normal mid-stem leaves: 5.

*Size.*—Large (6 inches by 4 inches).

*Quantity.*—Normal.

*Color.*—New foliage: Greyed-Purple Group 183A. Old foliage: Upper side: Green Group 136A; Lower side: Green Group 136C.

Leaflets:

*Shape.*—Pointed oval.

*Texture.*—Upper side: Glossy, smooth.

*Edge.*—Serrated.

*Serration.*—Single, small.

*Petiole rachis.*—Color: Reddish.

*Petiole underside.*—Rough, with prickles and glands.

*Stipules.*—Medium ½ inch), serrated.

*Disease Resistance.*—Resistant to mildew under normal greenhouse growing conditions at Somis, Calif.

Wood:

*New wood.*—Color: Light green. Bark: Smooth.

*Old wood.*—Color: Green. Bark: Smooth.

Prickles:

*Quantity.*—On main canes from base: Ordinary. On laterals from main canes: Ordinary.

*Form.*—Medium, hooked downward.

*Color when young.*—Red.

Small prickles:

*Quantity.*—On main stalks: Few. On laterals: Few.

*Color.*—Red.

I claim:

1. A new and distinct variety of rose plant of the hybrid tea class, substantially as herein shown and described, characterized particularly as to novelty by the unique combination of its coral orange flower color; its thick, leathery petals; its vigorous, upright habit of growth; its dark green, glossy foliage; and its good vase life.

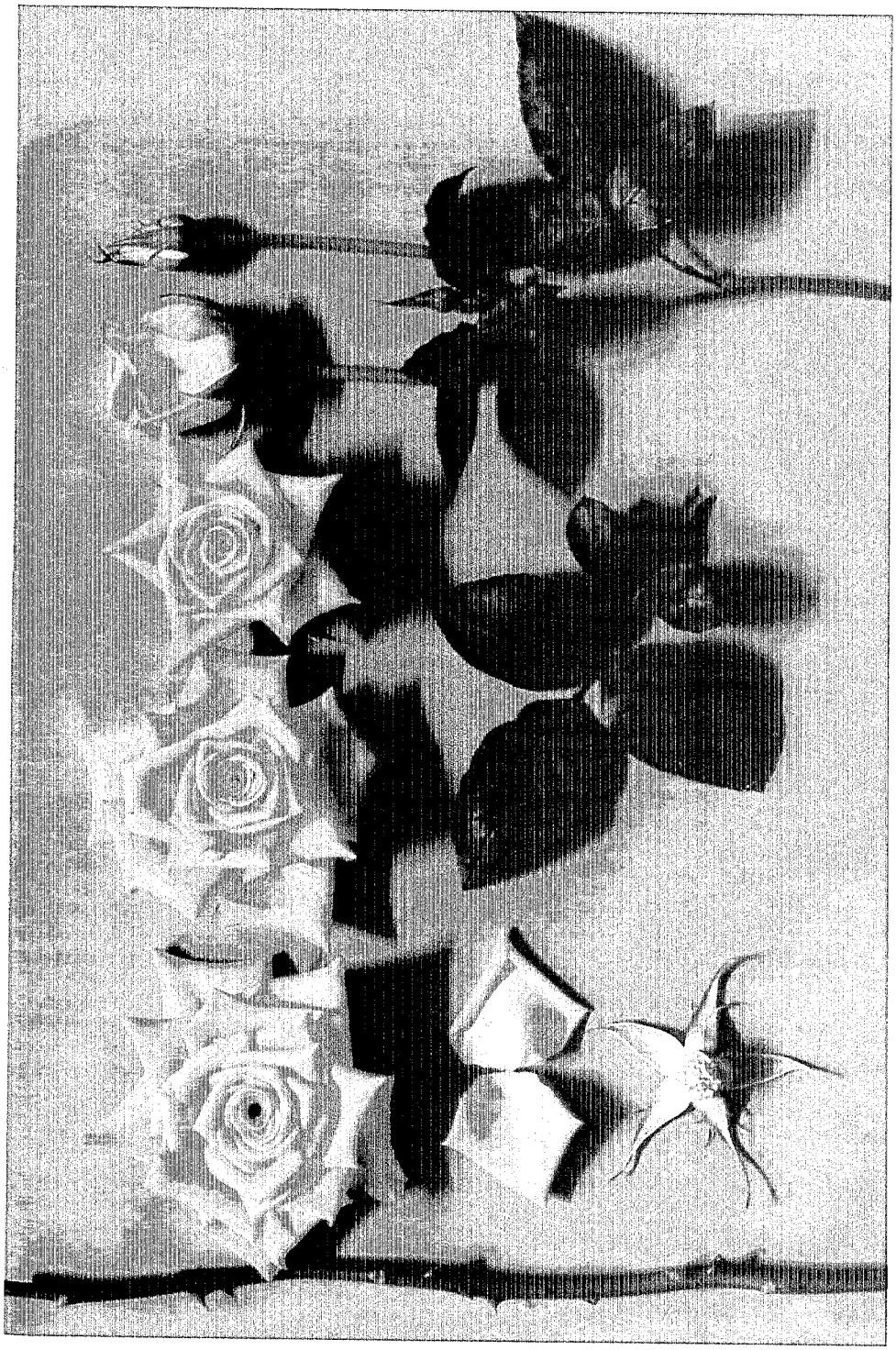

* * * * *